United States Patent [19]
Wurm et al.

[11] Patent Number: 5,484,720
[45] Date of Patent: Jan. 16, 1996

[54] METHODS FOR CALCIUM PHOSPHATE TRANSFECTION

[75] Inventors: Florian M. Wurm, Redwood City; Martin Jordan, San Bruno, both of Calif.

[73] Assignee: Genentech, Inc., South San Francisco, Calif.

[21] Appl. No.: 303,245

[22] Filed: Sep. 8, 1994

[51] Int. Cl.⁶ .................................................. C12N 15/64
[52] U.S. Cl. .................................... 435/172.3; 435/240.2
[58] Field of Search ...................... 435/172.3, 6, 240.2

[56] References Cited

U.S. PATENT DOCUMENTS 4,968,615  11/1990  Koszinowski et al. ............... 435/172.3

OTHER PUBLICATIONS

O'Mahoney and Adams, "Optimization of Experimental Variables Influencing Reporter Gene Expression in Hepatoma Cells Following Calcium Phosphate Transfection" *DNA and Cell Biology* 13(12):1227–1232 (1994).

Chang, P. L., "Calcium phosphate–mediated DNA transfection" *Gene Therapeutics: Methods and Applications of Direct Gene Transfer,* Jon A. Wolff, Boston:Birkhauser pp. 157–179 (1994).

Chen et al., "Calcium phosphate–mediated gene transfer: a highly efficient transfection system for stably transforming cells with plasmid DNA" *BioTechniques* 6(7):632–638 (1988).

Chen et al., "High–efficiency transformation of mammalian cells by plasmid DNA" *Molecular & Cellular Biology* 7(8):2745–2752 (1987).

Chu et al., "SV40 DNA transfection of cells in suspension: analysis of the efficiency of transcription and translation of T–antigen" *Gene* 13:197–202 (1981).

Czernilofsky et al., "Transformation of tobacco protoplasts by a Ca phosphate mediated precipitation technique and subsequent cellular concatemerization of the input DNA" *J. Cellular. Biochem.* Abstract Suppl.: p. 252, abs. No. 1776 (1985).

Donahue et al., "High efficiency DNA–mediated transformation of human diploid fibroblasts" *Oncogene* 3:221–224 (1988).

Graham et al., "A New Technique for the Assay of Infectivity of Human Adenovirus 5 DNA" *Virology* 52:456–467 (1973).

Ishiura et al., "Phage Particle–Mediated Gene Transfer to Cultured Mammalian Cells" *Molecular & Cellular Biology* 2(6):607–616 (1982).

Kjer et al., "Efficient transfection of mosquito cells is influenced by the temperature at which DNA–calcium phosphate coprecipitates are prepared" *Archives of Insect Biochem. Physiol.* 16:189–200 (1991).

Okayama et al., "Calcium phosphate mediated gene transfer into established cell lines" *Methods in Mol. Biol.,* E. J. Murray, Humana Press, Inc., Chapter 2, vol. 7:15–21 (1991).

Pasco et al., "Efficient DNA–mediated gene transfer into primary cultures of adult rat hepatocytes" *DNA* 8(7):535–541 (1989).

Steiner et al., "An automated method for calcium phosphate–mediated gene transfer" *Trends in Genetics* 5(5):138 (1989).

Wigler et al., "Biochemical transfer of single–copy eucaryotic genes using total cellular DNA as donor" *Cell* 14:725–731 (1978).

Wigler et al., "DNA–mediated transfer of the adenine phosphoribosyltransferase locus into mammalian cells" *Proc. Natl. Acad. Sci.* 76(3):1373–1376 (1979).

Xu et al., "High–efficiency gene transfer into cardiac myocytes" *Nucleic Acids Research* 20(23):6425–6426 (1992).

Yelle et al., "Efficient transfection of mammalian cells with viral DNA in optimal culture conditions" *J. Virol. Methods* 7(5–6):321–326 (1983).

Primary Examiner—Mindy B. Fleisher
Assistant Examiner—James Ketter
Attorney, Agent, or Firm—Richard B. Love

[57] ABSTRACT

A method is provided for calcium phosphate transfection of a eukaryotic host cell wherein particles comprising calcium phosphate and a desired nucleic acid are grown to an optimal size and then contacted with the host cell under conditions providing a substantially slower particle growth rate, thereby increasing the host cell's exposure to optimally-sized particles.

20 Claims, 8 Drawing Sheets

METHODS FOR CALCIUM PHOSPHATE TRANSFECTION

BACKGROUND OF THE INVENTION

1. Field of the Invention

This invention relates to the field of nucleic acid transfection, and more particularly to methods for nucleic acid transfection of eukaryotic cells by calcium phosphate co-precipitation.

2. Description of the Background and Related Art

The ability to introduce foreign DNA into eukaryotic host cells is one of the principle tools of recombinant DNA technology. Methods for transfecting eukaryotic host cells with foreign DNA can be broadly grouped into four categories: (1) direct introduction of cloned DNA by microinjection or microparticle bombardment; (2) use of viral vectors; (3) encapsulation within a carrier system; and (4) use of facilitators such as calcium phosphate and diethylaminoethyl (DEAE)-dextran. Of the reagents used as facilitators of DNA transfection, calcium phosphate remains the most widely used because of its simplicity and general effectiveness for a wide variety of cell types.

The original protocol for calcium phosphate transfection was described by Graham and van der Eb, *Virology*, 52: 456–467 (1973). This method was modified by Wigler et al., *Proc. Natl. Aced. Sci.*, 76:1373–1376 (1979) and by Chen and Okayama, *Mol, Cell. Biol.*, 7:2745–2752 (1987). Nevertheless, the original and modified protocols yield relatively low transfection efficiencies and expression in experiments geared towards transient or stable DNA transfer. Accordingly, there is still a need for an improved method of calcium phosphate transfection.

This and other objects will be apparent to those skilled in the art.

SUMMARY OF THE INVENTION

The invention provides for a method for introducing a desired nucleic acid into a eukaryotic host cell comprising admixing $Ca^{2+}$, $PO_4^{3-}$ and the desired nucleic acid to form a precipitation mixture; incubating the precipitation mixture to form particles comprising calcium phosphate and the desired nucleic acid, and allowing the particles grow to an average length of up to about 300 nanometers (nm); performing a step selected from the group consisting of: (1) diluting the precipitation mixture and simultaneously admixing the precipitation mixture to a eukaryotic host cell lacking a cell wall to form a transfection mixture with an initial $Ca^{2+}$ concentration that is at least ten fold lower than the initial $Ca^{2+}$ concentration of the precipitation mixture and wherein the particles are capable of further growth in the transfection mixture, and (2) diluting the precipitation mixture to form a diluted precipitation mixture, and thereafter admixing the diluted precipitation mixture to a eukaryotic host cell lacking a cell wall to form a transfection mixture with an initial $Ca^{2+}$ concentration that is at least ten fold lower than the initial $Ca^{2+}$ concentration of the precipitation mixture and wherein the particles are capable of further growth in the transfection mixture; and incubating the transfection mixture to allow the eukaryotic host cell to take up the particles to form a transfected cell.

The invention further provides a method for introducing a desired nucleic acid into a eukaryotic host cell comprising admixing $Ca^{2+}$, $PO_4^{3-}$ and the desired nucleic acid to form a precipitation mixture; incubating the precipitation mixture for a period of up to about 60 seconds to form a precipitate comprising calcium phosphate and the desired nucleic acid; performing a step selected from the group consisting of: (1) diluting the precipitation mixture and simultaneously admixing the precipitation mixture to a eukaryotic host cell lacking a cell wall to form a transfection mixture with an initial $Ca^{2+}$ concentration that is at least ten fold lower than the initial $Ca^{2+}$ concentration of the precipitation mixture and wherein the precipitate is capable of remaining insoluble in the transfection mixture, and (2) diluting the precipitation mixture to form a diluted precipitation mixture, and thereafter admixing the diluted precipitation mixture to a eukaryotic host cell lacking a cell wall to form a transfection mixture with an initial $Ca^{2+}$ concentration that is at least ten fold lower than the initial $Ca^{2+}$ concentration of the precipitation mixture and wherein the precipitate is capable of remaining insoluble in the transfection mixture; and incubating the transfection mixture to allow the eukaryotic host cell to take up the precipitate to form a transfected cell.

DETAILED DESCRIPTION OF THE PREFERRED EMBODIMENTS

A. DEFINITIONS

Figure 1:
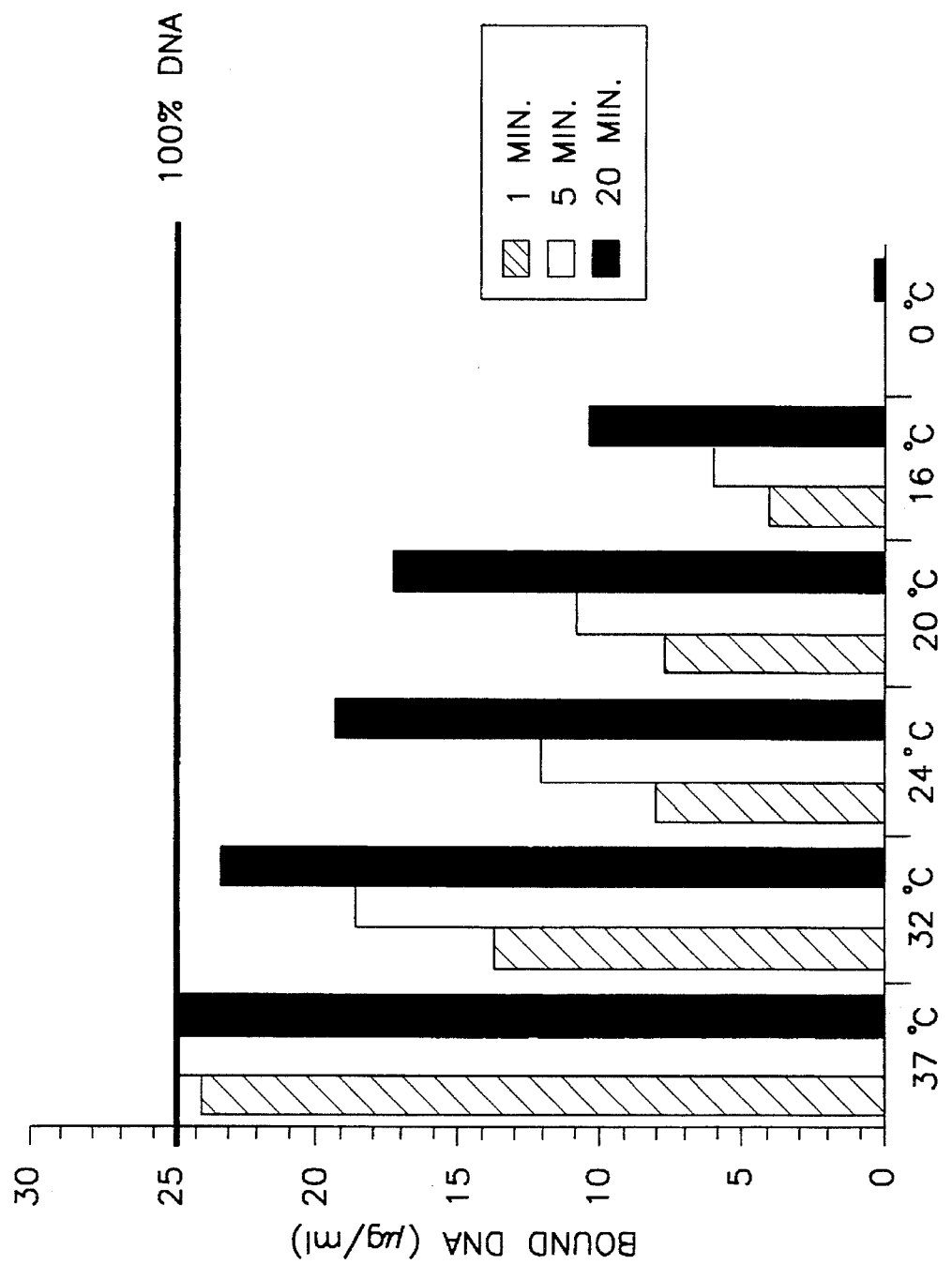
FIG. 1 is a graph depicting the effect of temperature and incubation time on the DNA binding capacity of a calcium phosphate precipitate formed with 25 micrograms per milliliter (μg/ml) DNA, 125 millimoles per liter (mM) $Ca^{2+}$ and 0.6 mM $PO_4^{3-}$. Shaded, open and closed columns represent incubation times of 1, 5 and 20 minutes, respectively.

As used herein, the term "transfection" is defined as the introduction of an extracellular nucleic acid into a host cell by any means known in the art, including calcium phosphate co-precipitation, viral transduction, liposome fusion, microinjection, microparticle bombardment, electroporation, etc. The terms "uptake of nucleic acid by a host cell", "taking up of nucleic acid by a host cell", "uptake of particles comprising nucleic acid by a host cell", and "taking up of particles comprising nucleic acid by a host cell" denote any process wherein an extracellular nucleic acid, with or without accompanying material, enters a host cell.

As used herein, the terms "nucleic acid-calcium phosphate co-precipitation" and "calcium phosphate co-precipitation" refer to a process wherein nucleic acid, $Ca^{2+}$, and $PC_4^{3-}$ in solution form insoluble particles, i.e., a precipitate, comprising hydroxyapatite (which has an approximate chemical formula of $(Ca_5OH(PO_4)_3)_2$, and is referred to herein as "calcium phosphate") and nucleic acid. Also included within the definition is the growth of such particles by further precipitation or by aggregation and/or rearrangement of such particles.

As used herein, the term "calcium phosphate transfection" refers to any method of transfecting a host cell wherein calcium phosphate is used to facilitate the uptake of nucleic acid by a host cell.

As used herein, the term "transformation" denotes introducing nucleic acid into a host cell so that the nucleic acid is replicable, either as a chromosomal integrant or as an extrachromosomal element.

As used herein, the term "eukaryotic host cell lacking a cell wall" refers to any nucleated cell which has no cell wall in the cell's native state, including all vertebrate cells, such as mammalian cells, avian cells, reptilian cells, amphibian cells, and fish cells, cells of multicellular invertebrate animals, such as insect cells, crustacean cells, and mollusk cells, cells of protozoans, etc., and to any nucleated cell which has had its native cell wall removed or is in a natural or artificially induced state wherein no cell wall is present, including all plant cells that are capable of forming protoplasts or are capable of being treated to form protoplasts.

As used herein, the term "desired nucleic acid" refers to any desired DNA, RNA or DNA/RNA hybrid.

As used herein, the term "desired DNA" is defined as any polydeoxynucleotide, including, e.g., double stranded DNA, single stranded DNA, double stranded DNA wherein one or both strands is (are) composed of two or more fragments, double stranded DNA wherein one or both strands has (have) an uninterrupted phosphodiester backbone, DNA containing one or more single stranded portion(s) and one or more double stranded portion(s), double stranded DNA wherein the DNA strands are fully complementary, double stranded DNA wherein the DNA strands are only partially complementary, circular, covalently closed DNA, linear DNA, covalently cross-linked DNA, cDNA, chemically synthesized DNA, semisynthetic DNA, biosynthetic DNA, naturally isolated DNA, enzyme digested DNA, sheared DNA, plasmid DNA, chromosomal DNA, labelled DNA, such as radiolabelled DNA and fluorochrome-labelled DNA, DNA containing one or more nonnaturally occuring species of nucleic acid, etc., that is selected for transfecting a host cell.

As used herein, the term "desired RNA" is defined as any polyribonucleotide, including, e.g., single stranded RNA, double stranded RNA, double stranded RNA wherein one or both strands is (are) composed of two or more fragments, double stranded RNA wherein one or both strands has (have) an uninterrupted phosphodiester backbone, RNA containing one or more single stranded portion(s) and one or more double stranded portion(s), double stranded RNA wherein the RNA strands are fully complementary, double stranded RNA wherein the RNA strands are only partially complementary, covalently cross-linked RNA, enzyme digested RNA, sheared RNA, mRNA, hnRNA, tRNA, including both charged and uncharged tRNA, rRNA, all forms of viral genomic RNA, chemically synthesized RNA, semisynthetic RNA, biosynthetic RNA, naturally isolated RNA, labelled RNA, such as radiolabelled RNA and fluorochrome-labelled RNA, RNA containing one or more nonnaturally occuring species of nucleic acid, etc., that is selected for transfecting a host cell.

As used herein, the terms "desired DNA/RNA hybrid" and "desired hybrid DNA/RNA" are defined as any hybrid nucleic acid comprising one strand of DNA and one strand of RNA wherein the DNA strand and the RNA strand form a species that is at least partially double stranded, including hybrids wherein the DNA strand is fully complementary or only partially complementary to the RNA strand, hybrids wherein the DNA strand and/or the RNA strand has (have) an uninterrupted phosphodiester backbone, hybrids wherein the DNA strand and/or the RNA strand is composed of two or more fragments, hybrids containing one or more single stranded portion(s) and one or more double stranded portion(s), hybrids created by reverse transcription of RNA, hybrids created by transcription of DNA, hybrids created by annealing of complementary or partially complementary DNA and RNA, covalently cross-linked hybrids, chemically synthesized hybrids, semisynthetic hybrids, biosynthetic hybrids, naturally isolated hybrids, labelled hybrids, such as radiolabelled hybrids and fluorochrome-labelled hybrids, hybrids containing one or more nonnaturally occuring species of nucleic acid, etc.

B. GENERAL METHODS

In general, the invention provides for improved methods of calcium phosphate transfection which exploit the heretofore unknown properties of nucleic acid-calcium phosphate co-precipitation and calcium phosphate facilitated nucleic acid transfection of host cells. In general, calcium phosphate transfection proceeds as follows. Nucleic acid associates strongly with the calcium phosphate particles formed in a calcium phosphate precipitate. In the presence of host cells, calcium phosphate particles carrying nucleic acid precipitate onto the host cell surface, and the nucleic acid enters the host cell. The present inventors discovered that there is a correlation between the host cell's ability to take up nucleic acid and the size of the nucleic acid-calcium phosphate particles, and that there is an optimum particle size that maximizes the host cell's ability to take up nucleic acid. As shown herein, the present inventors have determined that the optimum particle size is any size up to about 300 nm in length, wherein "length" is defined as the diameter at the widest part of the particle as measured by laser light scattering according to the method of Weiss and Frock, "Rapid Analysis of Particle Size Distribution by Laser Light Scattering", *Powder Technology*, 14:287 (1976). Thus, the methods of the invention are designed to maximize the host cell's uptake of nucleic acid by exposing the host cell to particles that have an average length of up to about 300 nm.

It is not possible to maintain calcium phosphate particles at a constant size because the particles are not stable in any liquid mixture. The particles either grow by precipitation, aggregation and rearrangement or dissolve, depending on the solubility of calcium phosphate in the mixture. Accordingly, the invention provides methods wherein the particles are grown to an optimal size in a nucleic acid-calcium phosphate co-precipitation step, the particles are diluted to lower the particle growth rate while maintaining particle insolubility, and the optimally sized particles are contacted with the host cell. The invention also provides methods wherein the particles are grown larger than the optimal size, reduced back down to the optimal size and contacted with the host cell.

A host cell can be exposed to the optimally sized particles in at least four ways: (1) forming the optimally-sized particles in a nucleic acid-calcium phosphate co-precipitate, and then diluting the co-precipitate and contacting it with the host cell in a single step by admixing the co-precipitate to a host cell culture; (2) forming the optimally-sized particles in a nucleic acid-calcium phosphate co-precipitate, diluting the co-precipitate, and then admixing the diluted co-precipitate to a host cell culture; (3) forming the optimally-sized particles in a host cell culture, and then diluting the host cell culture; and (4) forming particles that are larger than the optimal size, shrinking the particles back down to the optimal size and contacting the particles with the host cells.

I. Simultaneous Dilution of Co-Precipitate and Exposure to Host Cell a. Host Cell Preparation Any eukaryotic host cell lacking a cell wall can be used in the methods of the invention. Preferred for use herein are mammalian cells. Examples of useful mammalian host cell lines include monkey kidney CV1 line transformed by SV40 (COS-7, ATCC CRL 1651); human embryonic kidney line (293 or 293 cells subcloned for growth in suspension culture, Graham et el., *J. Gen Virol.*, 36:59 (1977)); baby hamster kidney cells (BHK, ATCC CCL 10); Chinese hamster ovary cells/—DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); monkey kidney cells (CV1 ATCC CCL 70); African green monkey kidney cells (VERO-76, ATCC CRL-1587); human cervical carcinoma cells (HELA, ATCC CCL canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51 ); TRI cells (Mather et al., *Annals N.Y. Acad. Sci.*, 383:44–68 (1982)); MRC 5 cells; FS4 cells; and a human hepatoma cell line (Hep G2).

The mammalian host cell of choice can be cultured by any method known in art, such as, e.g., growing the cells as a monolayer with Dulbecco modified Eagle medium (DMEM) supplemented with 10% calf serum in an incubator at 35° C. under a 5% $CO_2$ atmosphere. Other procedures can be used for particular cell types. For example, Drosophila cell lines can be grown as described by Di Nocera and Dawid, *Proc. Natl. Acad. Sci. USA*, 80:7095–7098 (1983) and fish cell lines can be grown as described by Araki et al., *Bull. Natl. Res. Inst. Aquaculture*, 20: 1–9 (1991).

Alternatively, a suspension cell culture can be used. Cells in suspension can be grown in spinner flasks, ranging in volume from 100 milliliters (ml) to 10 liters (L) or in bioreactors ranging in volume from 0.5 L to 10,000 L. Cells in a suspension culture must be kept in an exponential growth phase which can be achieved by several methods known in the art, the most common of which is subcultivation with fresh medium every 3 to 6 days. Standard techniques, methods and equipment are reviewed in Lubiniecki, ed, *Large Scale Mammalian Cell Culture Technology*, Marcel Dekker, New York and Basle, 1990.

In the case of plant cell hosts, the plant cell protoplast cultures suitable for use herein can be prepared according to the method of Lichtenstein and Draper, "Genetic Engineering of Plants", in *DNA Cloning Volume III: A Practical Approach*, Glover, ed, IRL Press (1985), pp.67–119.

b. DNA Preparation

Any desired DNA for use in the methods of the invention can be prepared by a variety of methods known in the art. These methods include, but are not limited to, chemical synthesis by any of the methods described in Engels et al., *Angew. Chem. Int. Ed. Engl.*, 28:716–734 (1989), the entire disclosure of which is incorporated herein by reference, such as the triester, phosphite, phosphoramidite and H-phosphonate methods. Alternatively, the desired DNA sequences can be obtained from existing clones or, if none are available, by screening DNA libraries and constructing the desired DNA sequences from the library clones.

Suitable quantities of DNA template for use herein can be produced by amplifying the DNA in well known cloning vectors and hosts, such as plasmid vectors carrying the pBR322 origin of replication for autonomous replication in most Gram-negative bacterial hosts, plasmid vectors carrying the pC194 (Ehrlich, *Proc. Natl. Acad. Sci, USA*, 7,5:1433–1436 (1978)) origin of replication for autonomous replication in Bacillus and some other Gram-positive bacterial hosts, or 2-micron circle (2 μ plasmid) vectors carrying an origin of replication for autonomous replication in most yeast hosts.

Alternatively, the DNA template can be amplified by polymerase chain reaction (PCR) as described by Saiki et al., *Sciences*, 230:1350 (1985), Mullis et al., *Cold Spring Harbor Symp. Quant. Biol.*, 51:263 (1986), Mullis and Faloona, *Methods Enzymol.*, 155:335 (1987), and Saiki et al., *Science*, 239:487 (1988).

c. RNA Preparation

Any desired RNA for use in the methods of the invention can be prepared by a variety of methods known in the art. These methods include, but are not limited to, chemical synthesis of RNA, and in vitro translation of a DNA template as described generally in *Current Protocols in Molecu-* lar Biology, Wiley Interscience, New York (1990).

Alternatively, the desired RNA can be isolated from total cellular RNA extracted from a host cell culture. Total cellular RNA can be isolated from the host cell culture by any method known in the art such as, in the case of RNA produced in mammalian host cells, the methods described by Favaloro et al., *Methods Enzymol.*, 65:718 (1980), Stallcup and Washington, *J. Biol. Chem.*, 258:2802 (1983), Birnboim, *Nucleic Acids Res.*, 16: 1487 (1988), Gilsin et al., *Biochemistry*, 13:2633 (1974), Ullrich et al., *Science*, 196:1313 (1977), Strohman et al., *Cell*, 10:265 (1977), and MacDonald et al., *Methods Enzymol.*, 152:219 (1987).

If the desired RNA is a polyadenylated mRNA fraction of total cellular RNA, the polyadenylated mRNA can be separated from the bulk of cellular RNA by affinity chromatography on oligodeoxythymidylate (oligo(dT))-cellulose columns using any method known in the art, such as the method of Edmonds et al., *Proc. Natl. Acad. Sci.*, 68: 1336 (1971) or the method of Aviv and Leder, *Proc. Natl. Acad. Sci.*, 69:1408 (1972).

If the size of the desired mRNA is known, the mRNA preparation can be further purified for mRNA molecules of the particular size by agarose gel electrophoresis of RNA in the presence of methylmercuric hydroxide as described in Lemischka et al., *J. Mol. Biol.*, 151: 101 (1981) or fractionation of RNA by sucrose density gradient centrifugation in the presence of methylmercuric hydroxide as described by Schweinfest et al., *Proc. Natl. Acad. Sci.*, 79:4997 (1982).

In addition, the desired RNA can be obtained from the recombinant or non-recombinant genome of an RNA virus, including single stranded RNA viruses, such as retroviruses, tobacco mosaic viruses, influenza viruses, Newcastle disease virus, and double stranded RNA viruses such as rotaviruses and rice dwarf virus. The desired RNA can be isolated by growing up the chosen RNA virus in a suitable host cell culture, harvesting the viral particles and then extracting the desired RNA from the viral particles. For example, the genomic RNA of Moloney's murine leukemia virus can be obtained according to the method of Schwartzberg et al., *Cell*, 37: 1043 (1984).

d. DNA/RNA Hybrid Preparation

The DNA/RNA hybrids suitable for use in the methods of the invention can be prepared by any method known in the art. In one embodiment, the DNA strand or DNA fragments is (are) produced as described in Section I(b) above, the RNA strand or fragments is (are) produced as described in Section I(c) above, and the DNA and RNA strands or fragments are admixed together and allowed to anneal. In another embodiment, the DNA/RNA hybrid can be produced by obtaining the desired DNA strand as described above, using the DNA strand as a template to drive synthesis of the complementary RNA strand by a DNA-directed RNA polymerase, and harvesting the DNA/RNA hybrid upon completion of the transcription reaction. Alternatively, the DNA/RNA hybrid can be obtained by obtaining the desired RNA strand as described above, using the RNA strand as a template to drive synthesis of the complementary DNA strand by a RNA-directed DNA polymerase, and harvesting the DNA/RNA hybrid upon completion of the reverse transcription reaction.

e. Procedure for calcium phosphate transfection

The invention encompasses any method for introducing a desired nucleic acid into a eukaryotic host cell wherein the desired nucleic acid, $Ca^{2+}$, and $PO_4^{3-}$ are admixed to form a precipitation mixture, the precipitation mixture is incubated to form particles comprising calcium phosphate and the desired nucleic acid and the particles are allowed to grow to an average length of up to about 300 nm, the precipitation mixture is simultaneously diluted and admixed to a eukaryotic host cells lacking a cell wall to form a transfection mixture wherein the particles are capable of further growth, and the transfection mixture is incubated to allow the host cell to take up the particles to form a transfected cell.

1. Formation of the Precipitation Mixture $Ca^{2+}$, $PO_4^{3-}$ and the desired nucleic acid can be admixed in any order to form a precipitation mixture wherein the nucleic acid co-precipitates with calcium phosphate. In one embodiment, the number of particles comprising nucleic acid and calcium phosphate formed in the precipitation mixture are maximized by admixing the nucleic acid to the precipitation mixture before or simultaneously with the admixture of $Ca^{2+}$ and $PO_4^{3-}$. The nucleic acid can be suspended in a buffer lacking both $Ca^{2+}$ and $PO_4^{3-}$ and then $Ca^{2+}$ and $PO_4^{3-}$ can be consecutively or simultaneously admixed to the nucleic acid suspension. Alternatively, the nucleic acid can be suspended in a buffer containing $Ca^{2+}$ or $PO_4^{3-}$ and then the appropriate counterion can be admixed to the nucleic acid suspension to initiate co-precipitation.

The concentration of reactants and the reaction conditions in the precipitation mixture are selected to produce particles comprising nucleic acid and calcium phosphate that have an average length of up to about 300 nm. In a preferred embodiment, the reactant concentrations and reaction conditions are selected to produce particles that have an average length of about 100 nm or less. The primary factors that determine particle formation are the kinetics of particle growth in the mixture and the reaction time. The rate of particle growth dictates the reaction time needed to attain the desired particle size. The rate of particle growth is dependent on the concentration of nucleic acid and the solubility of calcium phosphate in the mixture, and the calcium phosphate solubility, in turn, is dependent on the $Ca^{2+}$ concentration, $PO_4^{3-}$ concentration, pH, and temperature of the precipitation mixture.

The $Ca^{2+}$ concentration, $PO_4^{3-}$ concentration, pH, and temperature of the precipitation mixture are selected to provide a calcium phosphate solubility well below the actual $Ca^{2+}$ concentration and $PO_4^{3-}$ concentration in the mixture, thus providing a supersaturation of $Ca^{2+}$ and $PO_4^{3-}$ ions that drives co-precipitation of calcium phosphate and nucleic acid. Nucleic acid also affects the kinetics of particle growth in the supersaturated mixture because nucleic acid adheres to the surface of the particles, thereby slowing particle growth.

In the precipitation mixture, $Ca^{2+}$ can be present at an initial concentration of about 125 mM to about 375 mM, and preferably about 250 mM to about 375 mM, and $PO_4^{3-}$ can be present at an initial concentration of about 0.5 mM to about 1.0 mM and preferably about 0.75 mM. The higher $Ca^{2+}$ concentrations result in formation of particles with greater speed and frequency. Accordingly, the optimum nucleic acid concentration varies with the $Ca^{2+}$ concentration in the precipitation mixture. In DNA transfection embodiments using initial $Ca^{2+}$ concentrations of about 125 mM, 250 mM and 375 mM in the precipitation mixture, the initial DNA concentrations in the precipitation mixture can be up to about 25/μg/ml, 50/μg/ml, and 75/μg/ml, respectively. The pH of the precipitation mixture can be about 6.8 to about 7.6, and is preferably about 7.05. The temperature of the precipitation mixture can be about 0° C. to about 37° C., preferably about 20° C. to about 37° C., and more preferably about 32° C. to about 37° C.

Any pH buffer that is effective at a pH range encompassing the desired pH for the precipitation mixture can be used to suspend the reactants in the precipitation mixture. Buffers that are suitable for use herein include appropriate concentrations of N-3-hydroxyethylpiperazine-N'-3-ethanesulfonic acid (HEPES)-buffered saline, such as 25 mM HEPES and 140 mM NaCl, and appropriate concentrations of N,N-bis(3-hydroxyethyl)-3-aminoethanesulfonic acid (BES)-buffered saline, such as 25 mM BES and 140 mM NaCl.

The precipitation mixture is incubated for a period of time sufficient to allow particles comprising calcium phosphate and nucleic acid to grow to an average length of up to about 300 nm, and preferably an average length of about 100 nm or less. Under the reaction conditions described above, the particles formed in the precipitation mixture have an average length of about 300 nm or less after an incubation period of up to about 60 seconds. Accordingly, the precipitation mixture can be incubated for up to about 60 seconds. In a preferred embodiment, the precipitation mixture is incubated for a period of about 30 seconds or less.

2. Formation of the Transfection Mixture

After particles comprising calcium phosphate and the desired nucleic acid have grown to an average length of up to about 300 nm (or less) in the precipitation mixture, the precipitation mixture is simultaneously diluted and admixed to a eukaryotic host cell lacking a cell wall to form a transfection mixture. The eukaryotic cell is obtained in the form of an adherent cell culture or a suspension cell culture as described in section I(a) above. As provided herein, the precipitation mixture is diluted by admixture to the host cell culture such that the growth rate of the particles in the transfection mixture is substantially lowered, compared to the growth rate of the particles in the precipitation mixture, without allowing resolution of the particles, thereby maximizing the exposure of host cells to optimally sized particles.

In a preferred embodiment using a suspension cell culture, the precipitation and dilution steps are accomplished in an automated system wherein nucleic acid, $Ca^{2+}$, and $PO_4^{3-}$ are fed into an intake pipe that empties into the culture vessel. The flow rate through the intake pipe can be regulated to achieve the desired incubation period for nucleic acid-calcium phosphate co-precipitation to occur within the intake pipe. Preferably, the suspension culture is agitated to maximize the contact between host cells and optimally sized particles of calcium phosphate and nucleic acid.

In one embodiment, the transfection mixture has an initial $Ca^{2+}$ concentration that is at least ten-fold lower than the initial $Ca^{2+}$ concentration of the precipitation mixture. In a preferred embodiment, the precipitation mixture has an initial $Ca^{2+}$ concentration of about 250 mM to about 375 mM and the transfection mixture has an initial $Ca^{2+}$ concentration of about 12 mM.

Preferably, the particle growth rate is substantially reduced by the presence of serum or serum protein, such as bovine serum albumin, in the transfection mixture. Protein, like nucleic acid, associates strongly with the calcium phosphate particle surface and thereby impedes particle growth. In one embodiment, the transfection mixture contains about 2% to about 10% serum, such as fetal calf serum. In another embodiment, the transfection mixture contains about 0.2 grams per liter (g/L) to about 4 g/L serum albumin, such as bovine serum albumin.

The initial $PO_4^{3-}$ concentration of the transfection mixture used in the present methods can be conveniently provided by the $PO_4^{3-}$ present in the cell culture medium. Although other concentrations are also appropriate, the $PO_4^{3-}$ concentration of about 1 mM in serum-supplemented cell culture media is sufficient for use herein.

The pH and temperature of the transfection mixture are maintained at physiological levels tolerated by the host cells. In the case of mammalian host cells, it is desirable to maintain the pH in the range of about 6.0 to about 8.0 and the temperature in the range of about 15° C. to about 39° C. Similarly, the transfection mixture is incubated for a period of time that is easily optimized for the particular host cell.

In the case of transfection in a suspension cell culture, it is possible to precisely regulate the pH, $Ca^{2+}$ concentration, $PO_4^{3-}$ concentration and temperature such that the solubility of the particles comprising calcium phosphate and the desired nucleic acid is as high as possible without permitting resolvation of the particles. In a preferred embodiment, the transfection mixture is maintained at a pH of about 7.2 and a temperature of about 37° C. and the $Ca^{2+}$ concentration and the $PO_4^{3-}$ concentration therein are maintained such that the $PO_4^{3-}$ and $Ca^{2+}$ concentrations define a point that is above the calcium phosphate solubility curve shown in FIG. 7. In another preferred embodiment, the transfection mixture is maintained with a $PO_4^{3-}$ concentration of about 1 mM and a temperature of about 37° C. and the $Ca^{2+}$ concentration and pH are maintained such that the $Ca^{2+}$ concentration and pH define a point above the calcium phosphate solubility curve shown in FIG. 8.

Calcium phosphate precipitate is toxic to some host cells. Accordingly, it can be advantageous to dissolve the precipitate after the desired incubation period for transfection. The calcium phosphate precipitate in the transfection mixture can be dissolved, e.g., by lowering the pH and/or lowering the $Ca^{2+}$ concentration in the transfection mixture. The $Ca^{2+}$ concentration can be conveniently lowered by adding fresh culture medium to the transfection mixture.

For some host cells, an improved rate of transfection is obtained by shocking the transfection mixture with glycerol or dimethylsulfoxide (DMSO) at the end of the transfection incubation period. Typically, the transfection mixture is exposed to glycerol at a concentration of about 15% volume:volume for about 30 seconds to about 3 minutes, depending on the particular host cell, and then the cells are incubated in fresh medium for about 1 to 6 days.

Alternatively, following transfection the host cells can be cultured in fresh medium for the desired time period without a glycerol shock.

II. Dilution of Co-precipitate Followed by Exposure to the Host Cell

The invention also encompasses any method for introducing a desired nucleic acid into a eukaryotic host cell wherein the desired nucleic acid, $Ca^{2+}$, and $PO_4^{3-}$ are admixed to form a precipitation mixture, the precipitation mixture is incubated to form particles comprising calcium phosphate and the desired nucleic acid and the particles are allowed to grow to an average length of up to about 300 nm, the precipitation mixture is diluted to form a diluted precipitation mixture, the diluted precipitation mixture is admixed to a eukaryotic host cell lacking a cell wall to form a transfection mixture wherein the particles are capable of further growth, and the transfection mixture is incubated to allow the host cell to take up the particles to form a transfected cell.

a. Formation of the Precipitation Mixture

The precipitation mixture is obtained and incubated as described in Section I(e)(1) above. After the desired nucleic acid-calcium phosphate co-precipitate is formed, the precipitation mixture can be diluted by any convenient means, e.g., by adding an appropriate buffer or by adding the cell culture medium to be used in transfection. Buffers and media suitable for use herein are described in Sections I(a) and I(e)(1) above. The diluent is added to the precipitation mixture in an amount sufficient to reduce the rate of nucleic acid-calcium phosphate particle growth but not allow resolvation of such particles in the resulting diluted precipitation mixture.

Until it is admixed to a host cell to form a transfection mixture, the diluted precipitation mixture is maintained under conditions that permit continued but slow growth of the nucleic acid-calcium phosphate particles. Suitable conditions for obtaining a slow particle growth rate are set forth in the description of the transfection mixture in Section I(e)(2) above.

b. Formation of Transfection Mixture

As provided herein, the diluted precipitation mixture is admixed to a eukaryotic host cell lacking a cell wall to form a transfection mixture wherein the DNA-calcium phosphate particles will grow at a substantially lower rate than the particle growth rate in the precipitation mixture. The eukaryotic cell is obtained in the form of an adherent cell culture or a suspension cell culture as described in Section I(a) above, and the diluted precipitation mixture can be admixed to the cell culture to form a transfection mixture as described in Section I(e)(2) above.

The dilution of the particles in the diluted precipitation mixture and the dilution of the particles in the transfection mixture are chosen such that the overall dilution substantially lowers the particle growth rate without permitting the particles to dissolve. In a preferred embodiment, the overall dilution provides an initial $Ca^{2+}$ concentration in the transfection mixture that is at least ten-fold lower than the initial $Ca^{2+}$ concentration in the precipitation mixture.

In another preferred embodiment, most of the overall dilution occurs in the formation of the diluted precipitation mixture in order to slow down particle growth as soon as possible after the optimal particle size is attained.

Nevertheless, it will be appreciated that the invention also encompasses methods wherein the dilution that occurs in formation of the diluted precipitation mixture is small in comparison to the overall dilution in the transfection mixture. In such embodiments, it is preferable that the diluted precipitation mixture be quickly admixed to the host cell culture in order to attain a substantial decrease in particle growth rate before the average particle size exceeds the optimal range.

Alternatively, the percentage of the overall dilution that occurs in the formation of the diluted precipitation mixture and the percentage of the overall dilution that occurs in the formation of the transfection mixture can be varied according to the length of time between the two steps. A short time interval would permit the use of a smaller dilution in the diluted precipitation mixture whereas a longer time interval would necessitate the use of a larger dilution in the diluted precipitation mixture in order to prevent undue loss of transfection activity.

Preferably, the diluted precipitation mixture is immediately admixed to host cells in order to maximize the host cells' exposure to optimally sized nucleic acid-calcium phosphate particles. However, the invention also encompasses embodiments wherein the diluted precipitation mixture is maintained for any period of time before admixture to the host cells provided that the diluted precipitation mixture retains some ability to transfect the host cells at the time the transfection mixture is formed.

In a preferred embodiment using a suspension cell culture, the precipitation and dilution steps are accomplished in an automated system wherein nucleic acid, $Ca^{2+}$, and $PO_4^{3-}$ feed into an intake pipe that allows nucleic acid-calcium phosphate co-precipitation to occur, diluent feeds into the precipitation mixture through another intake pipe at some point downstream of the nucleic acid, $Ca^{2+}$, and $PO_4^{3-}$ intake, and thereafter the diluted precipitation mixture empties into the culture vessel. The flow rate through the intake pipe that carries the precipitation mixture and the downstream positioning of the diluent intake pipe can be adjusted to achieve the desired incubation period for the precipitation mixture and the desired delay between dilution of the precipitation mixture and admixture to the host cells in the culture vessel. Preferably, the suspension culture is agitated to maximize the contact between host cells and optimally sized particles of calcium phosphate and nucleic acid.

After it is formed, the transfection mixture can be incubated under the conditions described in Section I(e)(2) above.

III. Formation of Co-Precipitate in Host Cell Culture

The invention also encompasses any method for introducing a desired nucleic acid into a eukaryotic host cell wherein $Ca^{2+}$, $PO_4^{3-}$, nucleic acid, and a eukaryotic host cell lacking a cell wall are admixed to form a precipitation mixture, the precipitation mixture is incubated to form particles comprising calcium phosphate and the desired nucleic acid and the particles are allowed to grow to an average length of up to about 300 nm, the precipitation mixture is diluted to form a transfection mixture wherein the particles are capable of further growth, and the transfection mixture is incubated to allow the host cell to take up the particles to form a transfected cell.

a. Formation of the Precipitation Mixture

A suitable host cell culture can be obtained as described in Section I(a) above. The growth medium is removed from the cells, and the cells are exposed to appropriate concentrations of nucleic acid, $Ca^{2+}$, and $PO_4^{3-}$, described in Section I(e)(1) above, to form a precipitation mixture. It will be appreciated that the order of admixing nucleic acid, $Ca^{2+}$, and $PO_4^{3-}$ is not important for practicing the invention. The cells can be contacted with or suspended in a mixture containing any of the nucleic acid, $Ca^{2+}$, and $PO_4^{3-}$ components or combination thereof and then admixed to any missing component or components needed to complete the precipitation mixture. Alternatively, the cells can be admixed to all of the nucleic acid, $Ca^{2+}$, and $PO_4^{3-}$ components at once.

In a preferred embodiment, the precipitation mixture is formed by contacting the host cells with an appropriate serum-free growth medium which comprises the desired concentrations of nucleic acid, $Ca^{2+}$, and $PO_4^{3-}$. A medium containing serum or other proteins is undesirable for use in the precipitation mixture because proteins substantially reduce the growth of the nucleic acid-calcium phosphate co-precipitate.

The precipitation mixture reaction conditions and incubation period are selected to allow formation of optimally sized particles comprising calcium phosphate and nucleic acid as described in Section I(e)(1) above.

b. Formation Of the Transfection Mixture

After nucleic acid-calcium phosphate particles of the desired size are formed, the precipitation mixture is diluted to form a transfection mixture wherein the particles will grow at a substantially lower rate than the particle growth rate in the precipitation mixture. In one embodiment, the precipitation mixture is diluted by adding the appropriate serum-supplemented growth medium for the host cells. The resulting transfection mixture is incubated under conditions that allow the host cell to take up the nucleic acid-calcium phosphate particles to form a transfected cell. Such procedures are described in Section I(e)(2) above.

IV. Shrinking an Overgrown Co-Precipitate Followed by Exposure to the Host Cell The invention further encompasses any method for introducing a desired nucleic acid into a eukaryotic host cell wherein $Ca^{2+}$, $PO_4^{3-}$ and nucleic acid are admixed to form a precipitation mixture, the precipitation mixture is incubated to form particles comprising calcium phosphate and the desired nucleic acid and the particles are allowed to grow to an average length that is greater than about 300 nm, the particles are decreased in size to form optimally-sized particles with an average length of about 300 nm or less by incubating the precipitation mixture under conditions wherein the particles are capable of resolution, the optimally-sized particles are admixed to a eukaryotic host cell lacking a cell wall to form a transfection mixture, and the transfection mixture is incubated to allow the host cell to take up the particles to form a transfected cell.

a. Formation of the Overgrown Precipitate

An overgrown nucleic acid-calcium phosphate co-precipitate can be obtained by creating a precipitation mixture as described in Section I(e)(1) above and incubating the precipitation mixture under conditions that allow particles comprising calcium phosphate and nucleic acid to grow to an average length that is greater than about 300 nm. Under the reaction conditions described in Section I(e)(1) above, the particles formed in the precipitation mixture have an average length of about 300 nm or less after an incubation period of about 60 seconds. Accordingly, an overgrown precipitate can be formed by incubating the precipitation mixture for at least about 60 seconds.

b. Shrinking the Overgrown Precipitate

After the overgrown precipitate is formed in the precipitation mixture, the conditions in the precipitation mixture are altered to cause reduction of particle bulk in the precipitate. Since particle growth or shrinkage is dependent upon the solubility of calcium phosphate in the precipitation mixture, particle shrinkage can be achieved by increasing the solubility of calcium phosphate in the precipitation mixture. As described above, calcium phosphate solubility is determined by $Ca^{2+}$ concentration, $PO_4^{3-}$ concentration, pH and temperature. Calcium phosphate solubility can be increased by lowering the $Ca^{2+}$ concentration, lowering the $PO_4^{3-}$ concentration, lowering the pH and/or lowering the temperature of the precipitation mixture. In a preferred embodiment, the precipitation mixture is diluted with an appropriate buffer to lower the $Ca^{2+}$ and $PO_4^{3-}$ concentrations. In another embodiment, the dilution is performed by centrifuging the precipitation mixture and resuspending the pellet in an appropriate buffer to create an undersaturated solution of $Ca^{2+}$ and $PO_4^{3-}$. In yet another preferred embodiment, the pH of the precipitation mixture is lowered to create an undersaturated solution of $Ca^{2+}$ and $PO_4^{3-}$.

The precipitation mixture is incubated under conditions permitting shrinkage of the particles until the particles reach the optimal average length of about 300 nm or less, and preferably about 100 nm or less. The incubation period necessary to form optimally-sized particles varies according to the size of the overgrown particles immediately prior to shrinkage and the speed of resolution in the precipitation mixture. Thus, the incubation time is selected based on the amount of particle size reduction needed and the rate of particle shrinkage set by the $Ca^{2+}$ and $PO_4^{3-}$ undersaturation in the precipitation mixture.

c. Formation of Transfection Mixture

After the nucleic acid-calcium phosphate particles in the precipitation mixture are reduced to the optimal size, the conditions in the precipitation mixture are changed again to permit slow growth of the optimally-sized particles. In one embodiment, the precipitation mixture is admixed to a eukaryotic host cell lacking a cell wall to form a transfection mixture with an adequate $Ca^{2+}$ concentration, $PO_4^{3-}$ concentration, pH and temperature to permit the particles to grow at a slow rate as described in Section I(e)(2) above. In another embodiment, the $Ca^{2+}$ concentration, $PO_4^{3-}$ concentration, pH and temperature of the precipitation mixture, or any one or combination of these parameters, is (are) increased to attain a $Ca^{2+}$ and $PO_4^{3-}$ supersaturation level that permits the particles to grow at a slow rate and the precipitation mixture is admixed to a eukaryotic host cell lacking a cell wall to form a transfection mixture.

Lastly, the transfection mixture is incubated as described in Section I(e)(2) above,

V. Other Embodiments Involving Shrinkage of an Overgrown Co-Precipitate

In addition to methods for shrinking an overgrown precipitate prior to contacting the precipitate and the host cell, the invention also encompasses methods wherein the overgrown nucleic acid-calcium phosphate particles are simultaneously reduced in size and exposed to the host cell. In these embodiments, the precipitation mixture is simultaneously diluted and admixed to a host cell culture to form a transfection mixture wherein the particles are capable of decreasing in size and the transfection mixture is incubated under conditions wherein the particles are reduced until they reach an average length of about 300 nm or less, and preferably about 100 nm or less. The rate of particle resolvation (determined by the $Ca^{2+}$ concentration, $PO_4^{3-}$ concentration, pH, and temperature of the transfection mixture) and incubation time are selected to provide the desired amount of particle reduction as described in Section IV(b) above. Next, the conditions in the transfection mixture are changed to permit slow growth of the particles and the transfection mixture is incubated to allow the host cell to take up the particles to form a transformed host cell as described in Section IV(c) above.

Alternatively, an overgrown precipitate can be simultaneously diluted and admixed to a host cell culture to form a transfection mixture wherein the particles slowly decrease in size until they completely dissolve, which allows the host cell to take up the optimally sized particles that exist when the particles are reduced to an average length of 300 nm or less. In a preferred embodiment, the reduction in particle size is effected by allowing the transfection mixture to slowly lower its pH as a result of the $CO_2$ and lactate production of the host cells in culture. The gradual decrease in pH causes the transfection mixture to change from oversaturation of $Ca^{2+}$ and $PO_4^{3-}$ to an undersaturation of $Ca^{2+}$ and $PO_4^{3-}$, and the resulting slow rate of particle size reduction maximizes the time period during which host cells are exposed to optimally sized particles.

In another embodiment, the initial resolution of overgrown particles in the host cell culture is followed by repeated cycles of admixing fresh overgrown precipitate to the transfection mixture and dissolving the precipitate in the transfection mixture until the desired level of transfection is obtained.

Also encompassed herein are methods wherein the co-precipitation occurs in the host cell culture (as described in Section III above) and is allowed to continue until the particles are larger than the optimal size. In these embodiments, the overgrown particles are reduced back down to the optimal size by changing the culture conditions, and after optimal particle size is reached the culture conditions are changed again to permit slow growth of the particles and allow the host cell to take up the particles to form a transfected cell.

In addition, all of the methods described herein can be modified to incorporate a continuous cycle of particle overgrowth/particle reduction during incubation of the transfection mixture designed to maximize the amount of time that the host cells are exposed to optimally-sized particles. In a preferred embodiment using a suspension culture in a computer-controlled bioreactor, conditions in the transfection mixture are automatically altered according to an algorithm that estimates particle size and calculates the timing and degree of condition changes needed to achieve maximum cell contact with optimally-sized particles.

Further details of the invention can be found in the following examples, which further define the scope of the invention. All references cited herein are expressly incorporated by reference in their entirety.

EXAMPLE 1

Materials and Methods

1. Precipitation

Various amounts of purified plasmid DNA of the β-galactosidase expression vector pSVβ (Clontech, Palo Alto, CA) or of the tPA expression vector described in Refino et al., *Thrombosis and Hematosis*, 70:313–31 9 (1993) were diluted in a TE buffer (1 mM Tris(hydroxymethyl)aminomethane (Tris), 0.1 mM ethylenediamine-tetraacetic acid (EDTA), pH 7.6) solution containing concentrations of $CaCl_2$ that varied from 250 mM to 500 mM. One volume of the $DNA/CaCl_2$ solution was quickly added to one volume of a phosphate solution (50 mM HEPES, 280 mM NaCl, 1.5 mM $Na_2HPO_4$, pH 7.05) and the mixture was gently vortex mixed to initiate the formation of the precipitate. After various time periods of incubation at various temperatures, 300 µl aliquots of the mixture were microcentrifuged for 45 seconds and the optical densities of the supernatants were measured at 260 nm ($ID_{260}$) to quantify the amount of unbound DNA (an $OD_{260}$ of 1.0 corresponded to a DNA concentration of 50/µg/µl.)

2. Transfection

CHO cells (CHO-DUKX DHFR minus, Urlaub and Chasin, *Proc. Natl. Acad. Sci. USA*, 77:4216–4220 (1980)) and human kidney 293 cells (ATCC CRL1573) for transfections were passaged regularly every 3 to 4 days by subcultivation in T-flasks or in 500 ml spinner flasks using PSO4 medium, a medium proprietary to Genentech, Inc. (developed from the original formulations of Dulbecco's modified Eagle medium and Ham's F12 medium, catalog numbers 430-3000EB and 430– 1700EB in the 1990 catalog of Gibco BRL, Gaithersburg, MD 20877), containing 2% to 10% fetal calf serum. Cell cultures were conducted according to the general methods described in *Tissue Culture: Laboratory Procedures*, Doyle, Griffiths and Newell, eds, J. Wiley and Sons, New York (1992). One day prior to transfection, cells taken from exponentially growing cultures were seeded into 12 well plates at a density of $2 \times 10^5$ cells per well, 1 milliliter (ml) of growth medium supplemented with 2% to 10% fetal calf serum was added to each well, and the cell culture plates were incubated at 37° C. under a 5% $CO_2$ atmosphere for 24 hours.

The precipitation mixture was added to the individual wells (after various time periods of incubation at various temperatures) in volume:volume (v/v) ratios that resulted in a final $Ca^{2+}$ concentration of 12.5 mM. This maintained the condition of $Ca^{2+}$ and $PO_4^{3-}$ supersaturation if the pH was held at or above 7.2. CHO cells were exposed to the precipitate for 3 to 6 hours, shocked for 30 seconds with 15% glycerol, washed once and then incubated in fresh growth medium for 1 to 6 days. 293 cells were exposed to the precipitate for 3 to 20 hours and then incubated in fresh growth medium, without a glycerol shock, for 1 to 6 days.

Results and Discussion

A. Physico-chemical parameters of calcium phosphate DNA co-precipitate

1. Temperature

Figure 2:
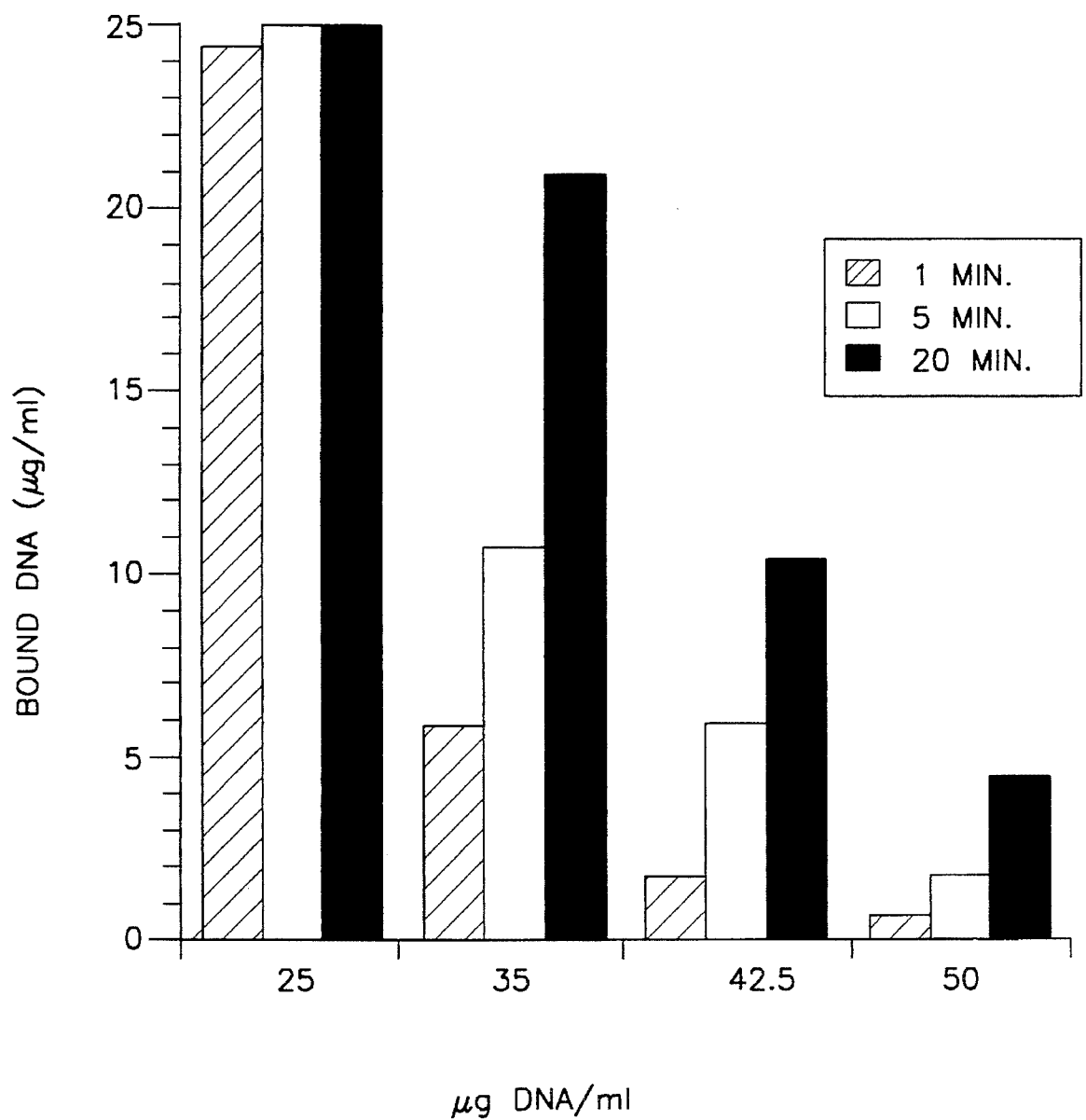
FIG. 2 is a graph depicting the effect of DNA concentration and incubation time on the DNA binding capacity of a calcium phosphate precipitate formed with 125 mM $Ca^{2+}$ and 0.75 mM $PO_4^{3-}$. Shaded, open and closed columns represent incubation times of 1, 5 and 20 minutes, respectively.

Although the heretofore disclosed calcium phosphate transfection protocols provide that DNA-calcium phosphate co-precipitation be carried out for at least 10 minutes, and most protocols recommend 20 minutes of co-precipitation, it was determined that under standard conditions (125 mM $Ca^{2+}$, 0.75 mM $PO_4^{3-}$, 25 µg/ml DNA, 20° C., pH 7.05) more than 95% of the DNA bound to the precipitate in less than 1 minute after admixture of the $DNA/CaCl_2$ solution to the phosphate solution (see the data for 25 µg/ml DNA in FIG. 2). To facilitate an investigation of the effect of temperature, the rate of crystal growth was reduced by using a lower phosphate concentration (0.6 mM $PO_4^{3-}$). The reduced rate of crystal growth permitted the binding of DNA to the precipitate to be observed over a period of 20 minutes at temperatures between 0° C. and 37° C. (FIG. 1 ). At 37° C., 100% of the DNA bound to the precipitate within 1 minute whereas at 0° C., all of the DNA remained in solution for 20 minutes. This result is due to the higher solubility of calcium phosphate at lower temperatures, which yields a less oversaturated solution with a lowered frequency of crystal nucleation.

2. DNA concentration

Since DNA concentration affects the transfection efficiency, the influence of DNA concentration on DNA-calcium phosphate co-precipitation was determined (FIG. 2). The precipitation was carried out at 20° C. with a phosphate concentration of 0.75 mM. The results demonstrated that an increase in the DNA concentration from 25 µg/ml to 50 µg/ml dramatically reduced the binding capacity of the precipitate (FIG. 2). At a concentration of 50/µg/ml, over 90% of the DNA remained in solution after 20 minutes and almost no pellet was found upon microcentrifugation for 45 seconds.

3. Calcium concentration

Figure 3:
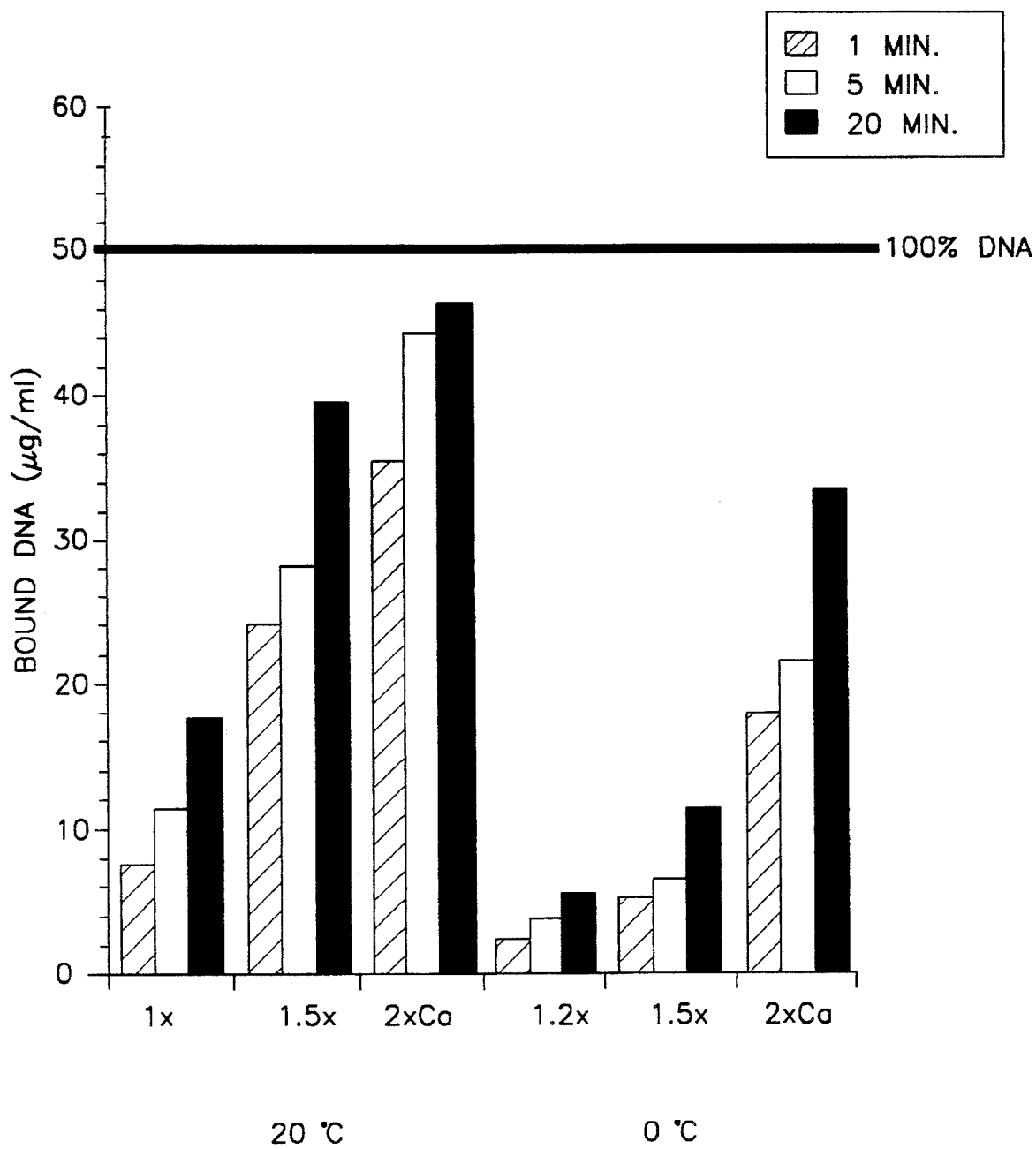
FIG. 3 is a graph depicting the effect of $Ca^{2+}$ concentration, incubation temperature and incubation time on the DNA binding capacity of a calcium phosphate precipitate formed with 50 μg/ml DNA and 0.75 mM $PO_4^{3-}$. The $Ca^{2+}$ concentrations denoted as "1×", "1.2×", "1.5×", and "2×Ca" correspond to 125 mM, 150 mM, 187.5 mM and 250 mM concentrations of $Ca^{2+}$, respectively. Shaded, open and closed columns represent incubation times of 1, 5 and 20 minutes, respectively.

Although $Ca^{2+}$ was present at a concentration that was 170-fold greater than the concentration of $PO_4^{3-}$ in the precipitation mixture, a further increase in $Ca^{2+}$ strongly affected the formation of a precipitate (FIG. 3). In the presence of 250 mM $Ca^{2+}$ and 50 µg/ml DNA, 30 to 45 µg/ml DNA was bound to a precipitate. Given that the absolute amount of precipitate was limited by the phosphate concentration (0.75 mM), a maximum of 125 µg of precipitate per ml was expected if all phosphate precipitated. The precipitate was found to bind up to 50 µg/ml of DNA in the presence of 375 mM $Ca^{2+}$ and 75 µg/ml DNA. Thus, DNA can account for approximately 40% of the mass of a precipitate that is formed under optimal conditions.

B. Transient Expression in CHO and 293 Cells

Figure 4:
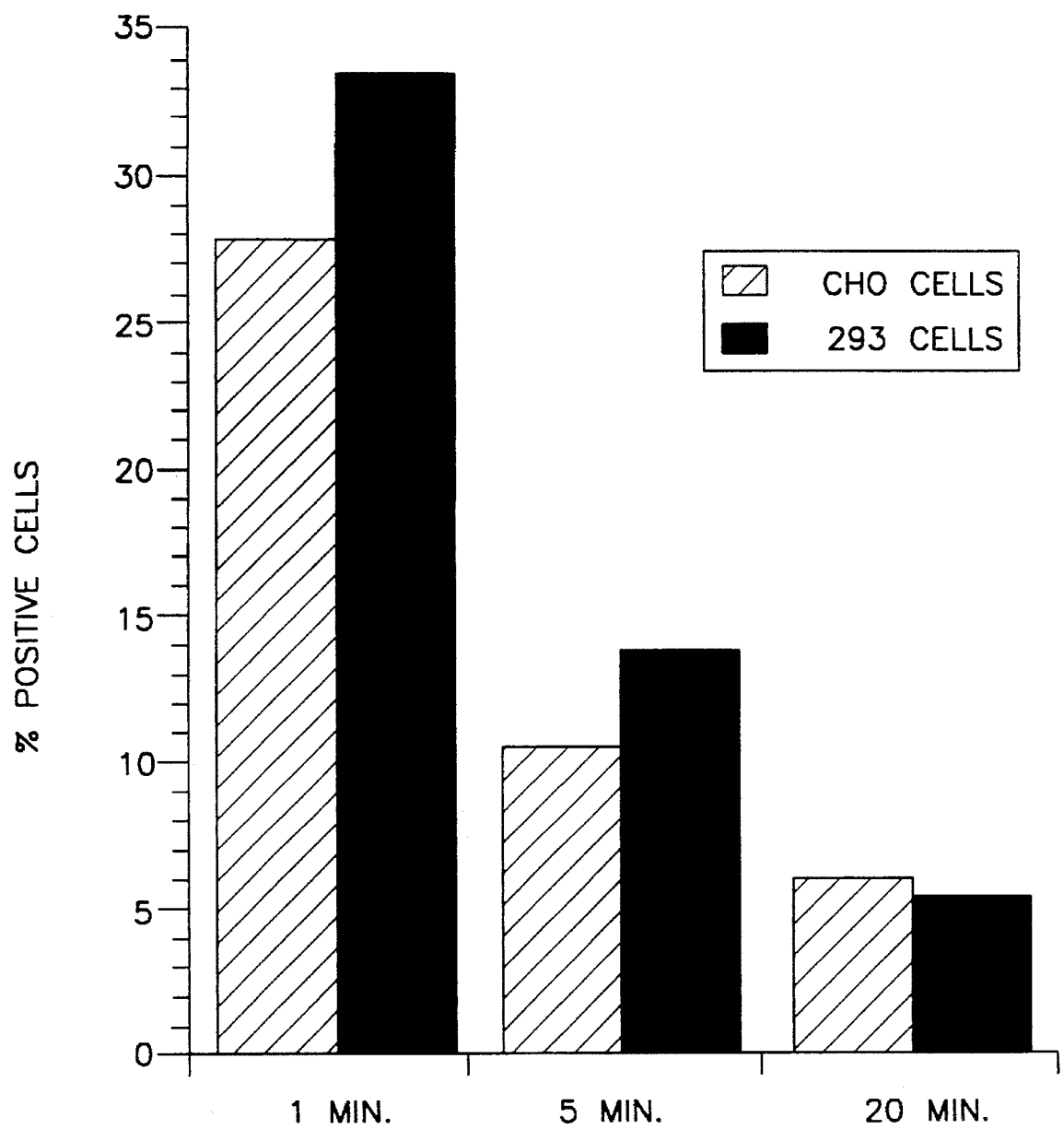
FIG. 4 is a graph depicting the effect of DNA-calcium phosphate co-precipitation incubation time on the transient expression of β-galactosidase in transfected CHO or 293 host cells as determined by the number of host cells that are positive for 5-bromo-4-chloro-3-indolyl-β-D-galactoside (X-gal) staining as a percentage of the total population of cells. The DNA-calcium phosphate co-precipitation was carried out with 25 μg/ml DNA, 125 mM $Ca^{2+}$, and 0.75 mM $PO_4^{3-}$. Shaded and closed columns represent Chinese hamster ovary (CHO) cell and human embryonic kidney 293 cell (293 cell) hosts, respectively.
Figure 5:
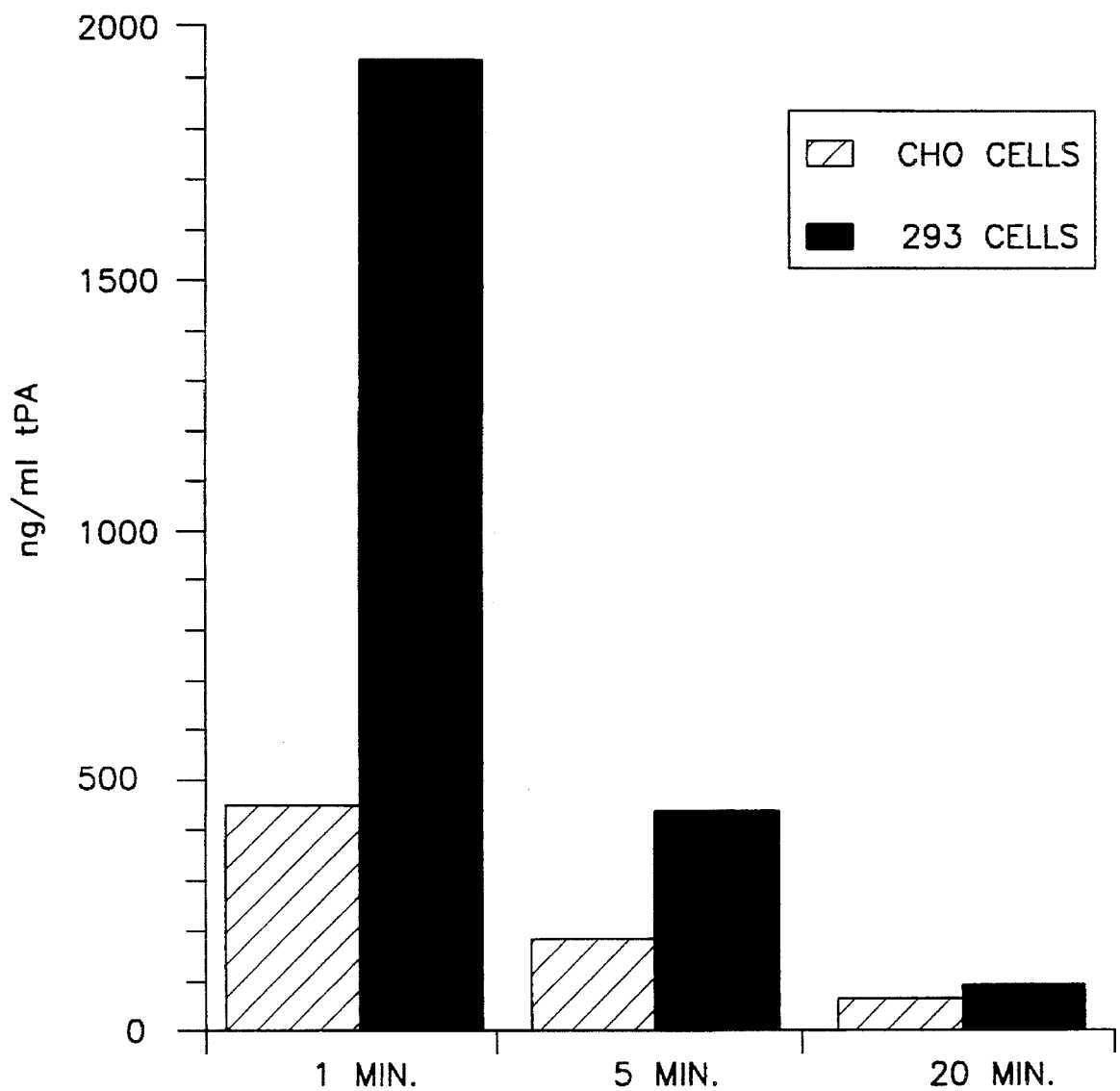
FIG. 5 is a graph depicting the effect of DNA-calcium phosphate co-precipitation incubation time on the transient expression of human tissue plasminogen activator (tPA) in transfected CHO or 293 cells as determined by the quantity of tPA detected in the cell culture supernatant by ELISA. The DNA-calcium phosphate co-precipitation was carried out with 25 μg/ml DNA, 125 mM $Ca^{2+}$, and 0.75 mM $PO_4^{3-}$. Shaded and closed columns represent CHO and 293 cell hosts, respectively.

The DNA-calcium phosphate co-precipitation was carried out under standard conditions (25 µg/ml DNA, 125 mM $Ca^{2+}$, 0.75 $PO_4^{3-}$). After incubation at 20° C. for various time periods, the precipitate was admixed to an exponentially growing cell culture. The transfection efficiency was analyzed either in an intracellular β-galactosidase expression system wherein expressing cells were identified by X-gel staining according to the method of Somes et al., *EMBO*, 5: 3133–3142 (1986) or in a tPA expression system wherein secreted tPA product was quantified with an ELISA assay according to the method of Bennet et al., *J. Biol. Chem.*, 266: 5191–5201 (1991). As shown in FIGS. 4 and 5, a one minute precipitation step produced the highest DNA transfection efficiency and expression level among the precipitation incubation periods tested. Inspection of the precipitates under a light microscope (phase contrast, 20× magnification) after 4 hours of exposure to the host cells showed that 1 minute of precipitation resulted in the formation of an enormous number of very small particles whereas 20 minutes of precipitation resulted in the formation of bigger but much fewer particles. The high transfection efficiency of the one-minute precipitates in both 293 cells and CHO cells is consistent with the above-described data showing that 1 minute of precipitation was sufficient to bind 100% of the DNA in a precipitation mixture with 25 µg/ml DNA, 125 mM $Ca^{2+}$ and 0.75 mM $PO_4^{3-}$.

Figure 6:
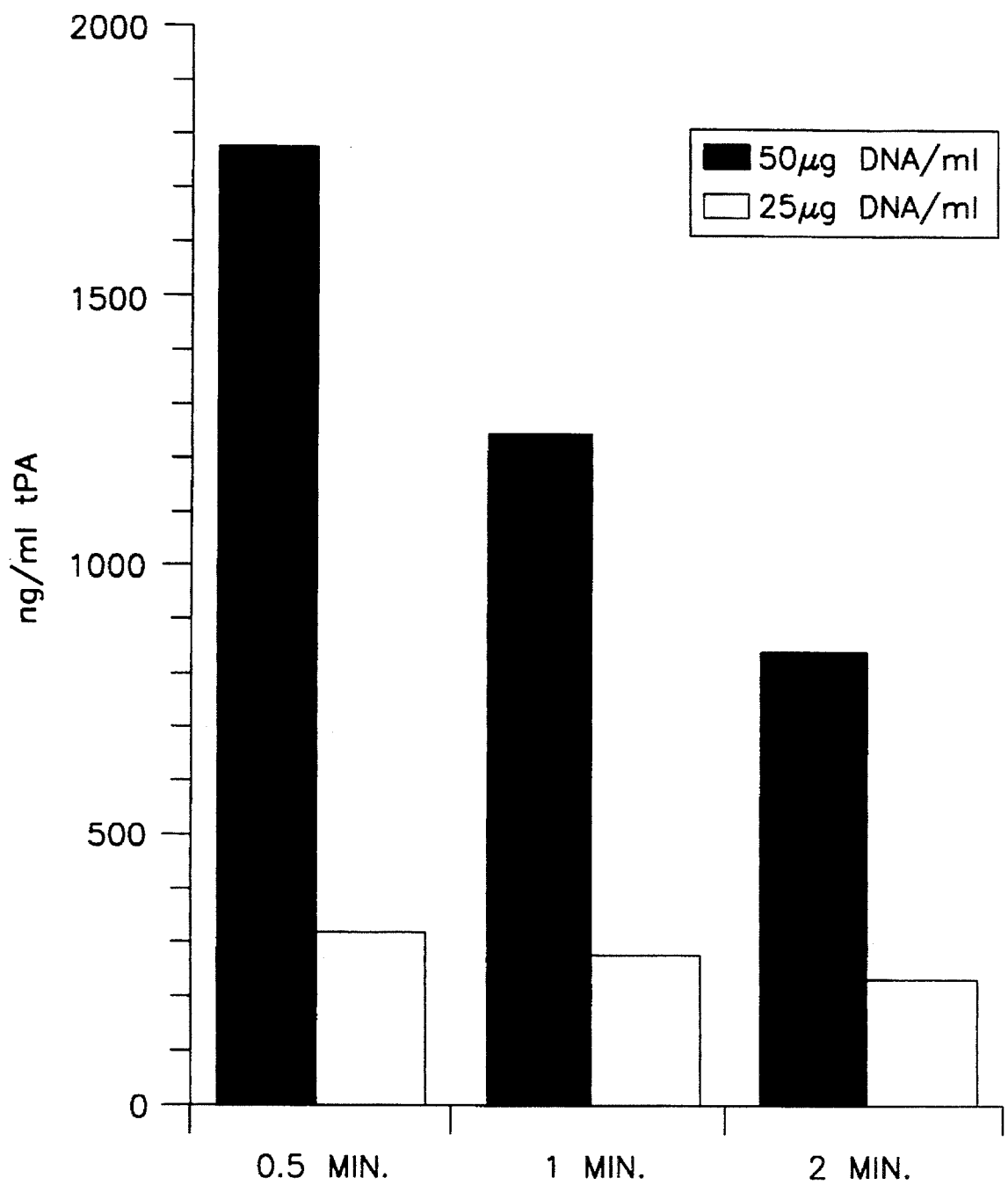
FIG. 6 is a graph depicting the effect of DNA-calcium phosphate co-precipitation incubation time on the transient expression of tPA in transfected CHO cells as determined by the quantity of tPA detected in the cell culture supernatant by ELISA. The DNA-calcium phosphate co-precipitation was carried out with 25 or 50 μg/ml DNA, 250 mM $Ca^{2+}$, and 0.75 mM $PO_4^{3-}$. Open and closed columns represent DNA concentrations of 25 and 50 μg/ml, respectively.

High levels of transient expression were achieved by using a $Ca^{2+}$ concentration of 250 mM (which maximized the frequency of the crystal nucleation event) and a DNA concentration of 50 µg/ml (which saturated the growing crystals). The crystal size was controlled by admixing the precipitate to the cells after very short incubation periods as shown in FIG. 6. Under these conditions, tPA product titers obtained in CHO host cells were as high as 2 µg/ml, and were routinely above 1/µg/ml, 3 days after transfection. 293 cells also produced higher transient expression levels after transfection with precipitates formed in 30 seconds with 250 mM $Ca^{2+}$ and 50 µg/ml DNA. Under these conditions, 293 cells yielded 5 µg/ml of tPA 2 days after transfection with a transient specific productivity of about 2 µg/$10^6$ cells/day.

EXAMPLE 2

Materials and Methods

In a first matrix plate test, various concentrations of $PO_4^{3-}$ (between 0.4 mM and 2.5 mM) were combined with various concentrations of $Ca^{2+}$ (between 2 mM and 10 mM) in 1 ml of 140 mM NaCl, 30 mM HEPES, pH 7.2. The plates were incubated overnight at 37° C. Each well was examined under a light microscope (phase contrast, 20× magnification) and scored for the presence of a precipitate.

In a second matrix plate test, various concentrations of $Ca^{2+}$ (between 4.2 mM and 18.0 mM) were combined with 1 ml of 30 mM HEPES and 0.95 mM $PO_4^{3-}$ in PSO4 medium at a various pH's (between 6.8 and 7.6). The mixtures were incubated overnight at 37° C. Each well was examined under a light microscope (phase contrast, 20× magnification) and scored for the presence of a precipitate.

Results and Discussion

Figure 7:
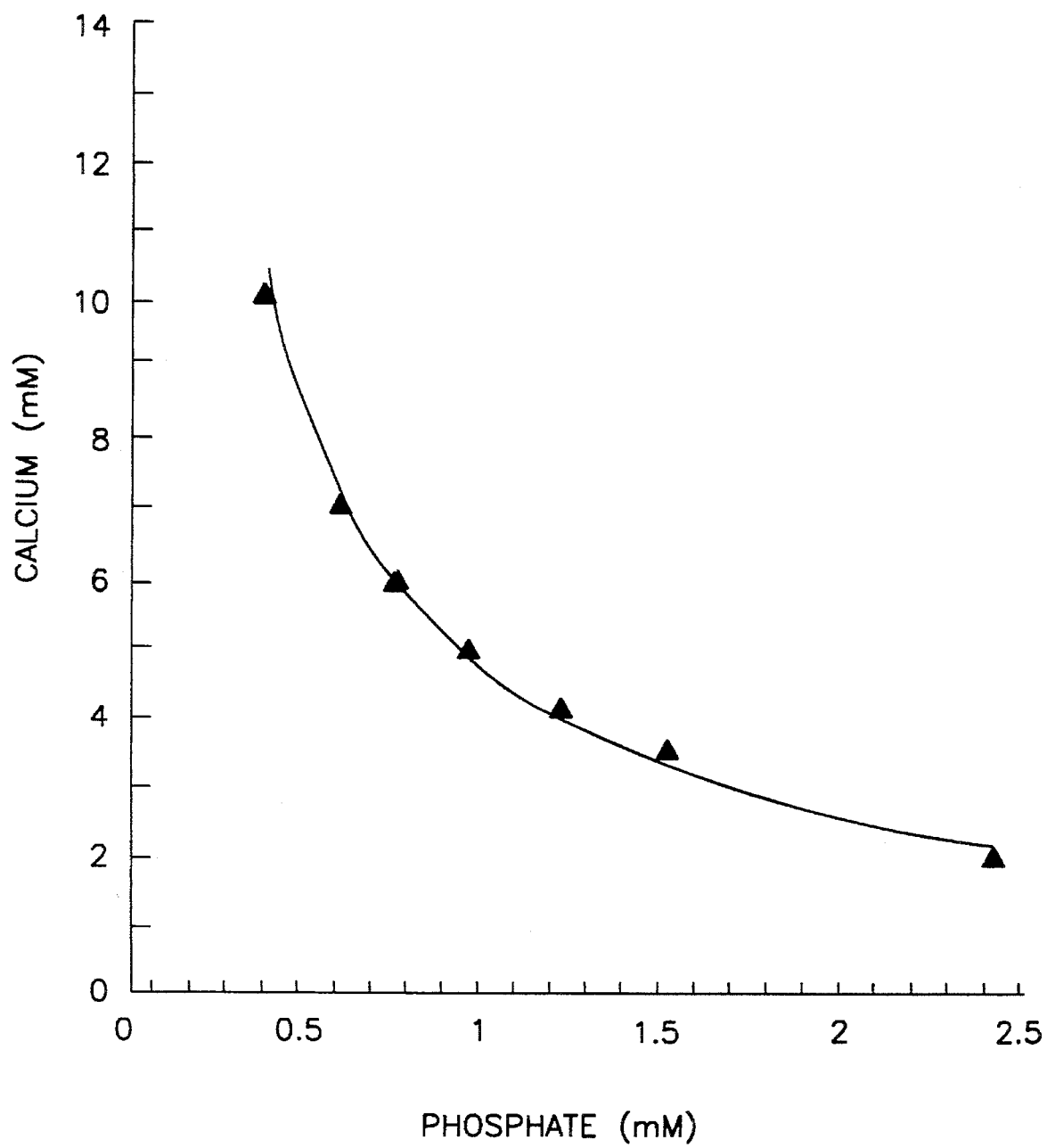
FIG. 7 is a graph depicting the solubility of calcium phosphate as a function of $Ca^{2+}$ concentration and $PO_4^{3-}$ concentration in a solution containing 140 mM NaCl, 30 mM N-3-hydroxyethylpiperazine-N'-3-ethanesulfonic acid (HEPES), pH 7.2 at 37° C.

The data produced in the first set of tests are summarized in FIG. 7. The data points on the curve in FIG. 7 represent the lowest concentrations of $Ca^{2+}$ and $PO_4^{3-}$ that produced a precipitate. Thus, the data points appearing in FIG. 7 define a calcium phosphate solubility curve as a function of $Ca^{2+}$ concentration and $PO_4^{3-}$ concentration. Using a regression with the method of least squares, the solubility of calcium phosphate as a function of $Ca^{2+}$ concentration and $PO_4^{3-}$ concentration was found to be approximated by the equation $y=(4.704)(x^{-0.82699})$, where y is the $Ca^{2+}$ concentration and x is the $PO_4^{3-}$ concentration. At any point (x,y) above the curve, the calcium phosphate particles are capable of continued growth. At any point (x,y) below the curve, the precipitate quickly redissolves.

Figure 8:
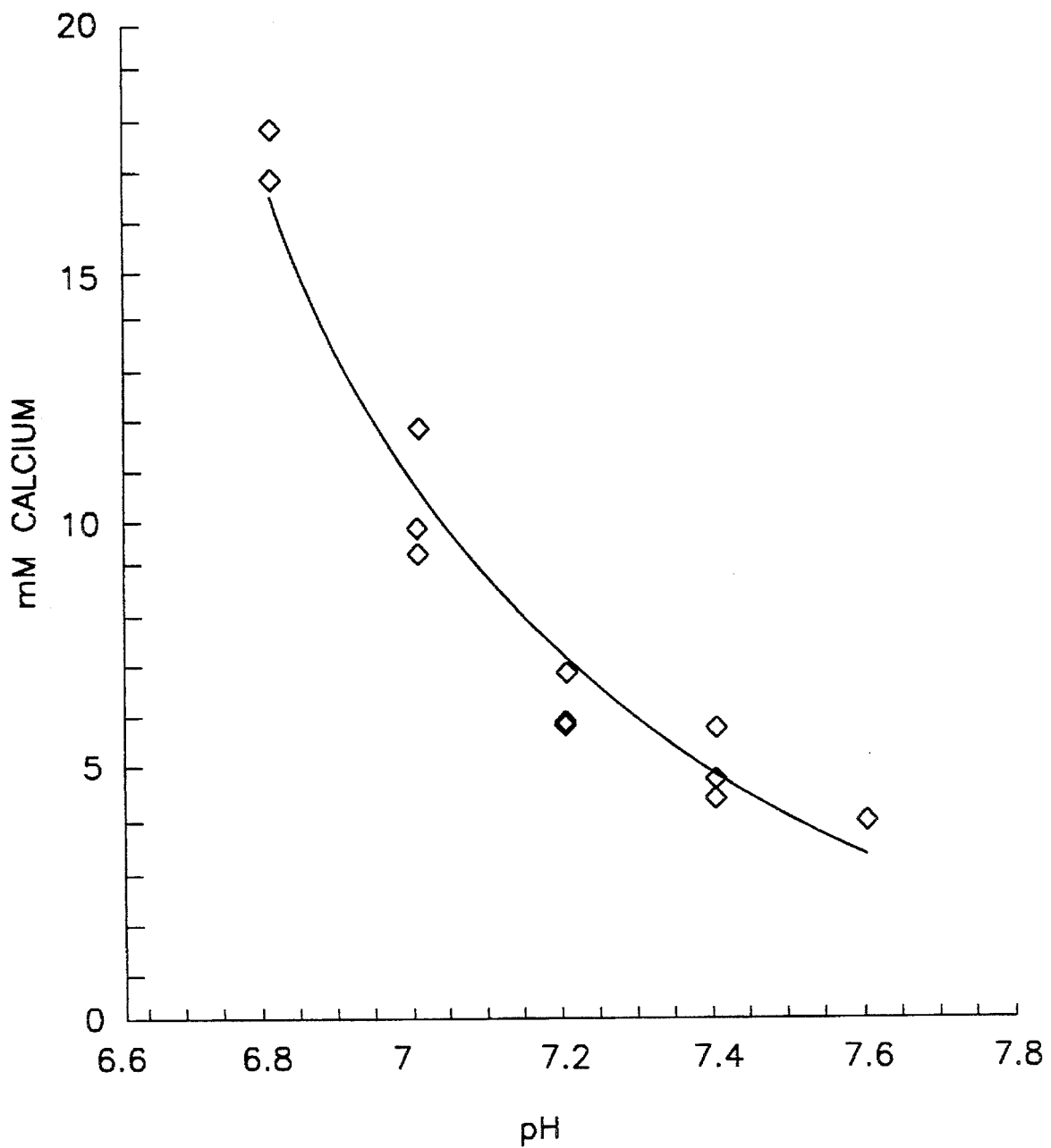
FIG. 8 is a graph depicting the solubility of calcium phosphate as a function of $Ca^{2+}$ concentration and pH in a solution containing 30 mM HEPES and 0.95 mM $PO_4^{3-}$ in PSO4 medium at 37° C.

The data produced in the second set of tests are summarized in FIG. 8. The data points on the curve in FIG. 8 represent the lowest $Ca^{2+}$ concentrations and pH's that produced a precipitate. Thus, the data points appearing in FIG. 8 define a calcium phosphate solubility curve as a function of $Ca^{2+}$ concentration and pH. Using a regression with the method of least squares, the solubility of calcium phosphate as a function of $Ca^{2+}$ concentration and pH was found to be approximated by the equation $y=(8.6886)(10^{12})(x^{-14.075})$, where y is the $Ca^{2+}$ concentration and x is the pH. At any point (x,y) above the curve, the calcium phosphate particles are capable of continued growth. At any point (x,y) below the curve, the precipitate quickly redissolves.

We claim:

1. A method for introducing a desired nucleic acid into a eukaryotic host cell, comprising (a) admixing $Ca^{2+}$, $PO_4^{3-}$ and the desired nucleic acid to form a precipitation mixture;

(b) incubating the precipitation mixture to form particles comprising calcium phosphate and the desired nucleic acid, and allowing the particles to grow to an average length of up to about 300 nm;

(c) performing a step selected from the group consisting of: (1) diluting the precipitation mixture and simultaneously admixing the precipitation mixture with a eukaryotic host cell lacking a cell wall to form a transfection mixture with an initial $Ca^{2+}$ concentration that is at least ten fold lower than the initial $Ca^{2+}$ concentration of the precipitation mixture in step (a) and wherein the particles are capable of further growth; and (2) diluting the precipitation mixture to form a diluted precipitation mixture, and thereafter admixing the diluted precipitation mixture with a eukaryotic host cell lacking a cell wall to form a transfection mixture with an initial $Ca^{2+}$ concentration that is at least ten fold lower than the initial $Ca^{2+}$ concentration of the precipitation mixture in step (a) and wherein the particles are capable of further growth; and (d) incubating the transfection mixture to allow the eukaryotic host cell to take up the particles to form a transfected cell.

2. The method of claim 1 wherein in step (b) the particles are allowed to grow to an average length of up to about 100 nm.

3. The method of claim 1 wherein the eukaryotic host cell is a mammalian cell.

4. The method of claim 1 wherein in step (b) the precipitation mixture is incubated for a period of up to about 60 seconds.

5. The method of claim 4 wherein in step (b) the precipitation mixture is incubated for a period of up to about 30 seconds.

6. The method of claim 1 wherein the desired nucleic acid is DNA.

7. The method of claim 6 wherein in step (a) the precipitation mixture comprises an initial $Ca^{2+}$ concentration of about 250 mM.

8. The method of claim 7 wherein in step (a) the precipitation mixture comprises an initial concentration of the desired DNA of about 50 μg/ml.

9. The method of claim 6 wherein in step (a) the precipitation mixture comprises an initial $Ca^{2+}$ concentration of about 375 mM and an initial concentration of the desired DNA of about 75/μg/ml.

10. The method of claim 1 wherein in step (d) the transfection mixture comprises a pH of about 7.2, a $Ca^{2+}$ concentration equal to a value y expressed as millimoles per liter (mM), and a $PO_4^{3-}$ concentration equal to a value x expressed as mM, wherein y is about 2.0 to about 20.0, x is about 0.4 to about 2.5, and y is greater than $(4.704)(x^{-0.82699})$.

11. The method of claim 1 wherein in step (d) the transfection mixture comprises a $PO_4^{3-}$ concentration of about 1.0 mM, a $Ca^{2+}$ concentration equal to a value y expressed as millimoles per liter (mM) and a pH equal to a value x expressed as $-\log_{10}$(moles of $H^+$ per liter), wherein y is about 3.0 to about 20.0, x is about 6.8 to about 7.8, and y is greater than $(8.6886)(10^{12})(x^{-14.075})$.

12. A method for introducing a desired nucleic acid into a eukaryotic host cell, comprising (a) admixing $Ca^{2+}$, $PO_4^{3-}$ and the desired nucleic acid to form a precipitation mixture;

(b) incubating the precipitation mixture for a period of up to about 60 seconds to form a precipitate comprising calcium phosphate and the desired nucleic acid;

(c) performing a step selected from the group consisting of: (1) diluting the precipitation mixture and simultaneously admixing the precipitation mixture to a eukaryotic host cell lacking a cell wall to form a transfection mixture with an initial $Ca^{2+}$ concentration that is at least ten fold lower than the initial $Ca^{2+}$ concentration of the precipitation mixture in step (a) and wherein the precipitate is capable of remaining insoluble; and (2) diluting the precipitation mixture to form a diluted precipitation mixture, and thereafter admixing the diluted precipitation mixture to a eukaryotic host cell lacking a cell wall to form a transfection mixture with an initial $Ca^{2+}$ concentration that is at least ten fold lower than the initial $Ca^{2+}$ concentration of the precipitation mixture in step (a) and wherein the precipitate is capable of remaining insoluble; and (d) incubating the transfection mixture to allow the eukaryotic host cell to take up the precipitate to form a transfected cell.

13. The method of claim 12 wherein the eukaryotic host cell is a mammalian cell.

14. The method of claim 12 wherein in step (b) the precipitation mixture is incubated for a period of up to about 30 seconds.

15. The method of claim 12 wherein the desired nucleic acid is DNA.

16. The method of claim 15 wherein in step (a) the precipitation mixture comprises an initial $Ca^{2+}$ concentration of about 250 mM.

17. The method of claim 16 wherein in step (a) the precipitation mixture comprises an initial concentration of the desired DNA of about 50 μg/ml.

18. The method of claim 15 wherein in step (a) the precipitation mixture comprises an initial $Ca^{2+}$ concentration of about 375 mM and an initial concentration of the desired DNA of about 75 μg/ml.

19. The method of claim 12 wherein in step (d) the transfection mixture comprises a pH of about 7.2, a $Ca^{2+}$ concentration equal to a value y expressed as millimoles per liter (mM), and a $PO_4^{3-}$ concentration equal to a value x expressed as mM, wherein y is about 2.0 to about 20.0, x is about 0.4 to about 2.5, and y is greater than $(4.704)(x^{-0.82699})$.

20. The method of claim 12 wherein in step (d) the transfection mixture comprises a $PO_4^{3-}$ concentration of about 1.0 mM, a $Ca^{2+}$ concentration equal to a value y expressed as millimoles per liter (mM) and a pH equal to a value x expressed as $-\log_{10}$(moles of $H^+$ per liter), wherein y is about 3.0 to about 20.0, x is about 6.8 to about 7.8, and y is greater than $(8.6886)(10^{12})(x^{-14.075})$.

* * * * *